United States Patent [19]
Koch

[11] Patent Number: 5,902,314
[45] Date of Patent: May 11, 1999

[54] MEDICAL INSTRUMENT FOR REMOVING LUMEN OBSTRUCTIONS

[76] Inventor: Craig S. Koch, 6176 Reservoir Ct., Granite Bay, Calif. 95746

[21] Appl. No.: 09/010,407

[22] Filed: Jan. 22, 1998

[51] Int. Cl.⁶ .................................................. A61B 17/22
[52] U.S. Cl. .......................................... 606/160; 606/162
[58] Field of Search .................................. 606/160, 161, 606/162, 107, 110, 113, 114

[56] References Cited

U.S. PATENT DOCUMENTS

| | | | |
|---|---|---|---|
| 879,297 | 2/1908 | Moormeister | 606/160 |
| 928,011 | 7/1909 | Whitlock | 606/160 |
| 5,451,230 | 9/1995 | Steinert | 606/161 |

*Primary Examiner*—Michael Buiz
*Assistant Examiner*—Kevin Truong
*Attorney, Agent, or Firm*—Donald E. Nist

[57] ABSTRACT

The improved medical instrument is adapted to remove obstructions from ear canals, nostrils and endotracheal tube airways. It includes an elongated handle with an elongated hollow tube connected to the front end thereof and an elongated flexible wire extending from the front end of the tube. The front end of the wire is curved to form a scoop for removing obstructions from a lumen. In one embodiment the wire and tube are removable as a replaceable unit from the front end of the handle. In another embodiment the handle has a central cavity therein communicating with the cavity in the tube and through both of which the wire extends. The wire is connected to a spring which extends out of the handle. The spring biases the wire into the tube. When the wire is manually depressed the front end of the wire extends out of tube and curves into the desired scoop configuration. The instrument can include a light which is switched on when the wire extends out of the tube and which is used to light the lumen. In another embodiment the front end of the wire forms a loop which goes back into the tube, which is flexible, the loop being extendable from the tube by spring biasing. In a further embodiment one end of the loop is secured to the exterior of the tube and the loop is shielded by a removable cap.

2 Claims, 3 Drawing Sheets

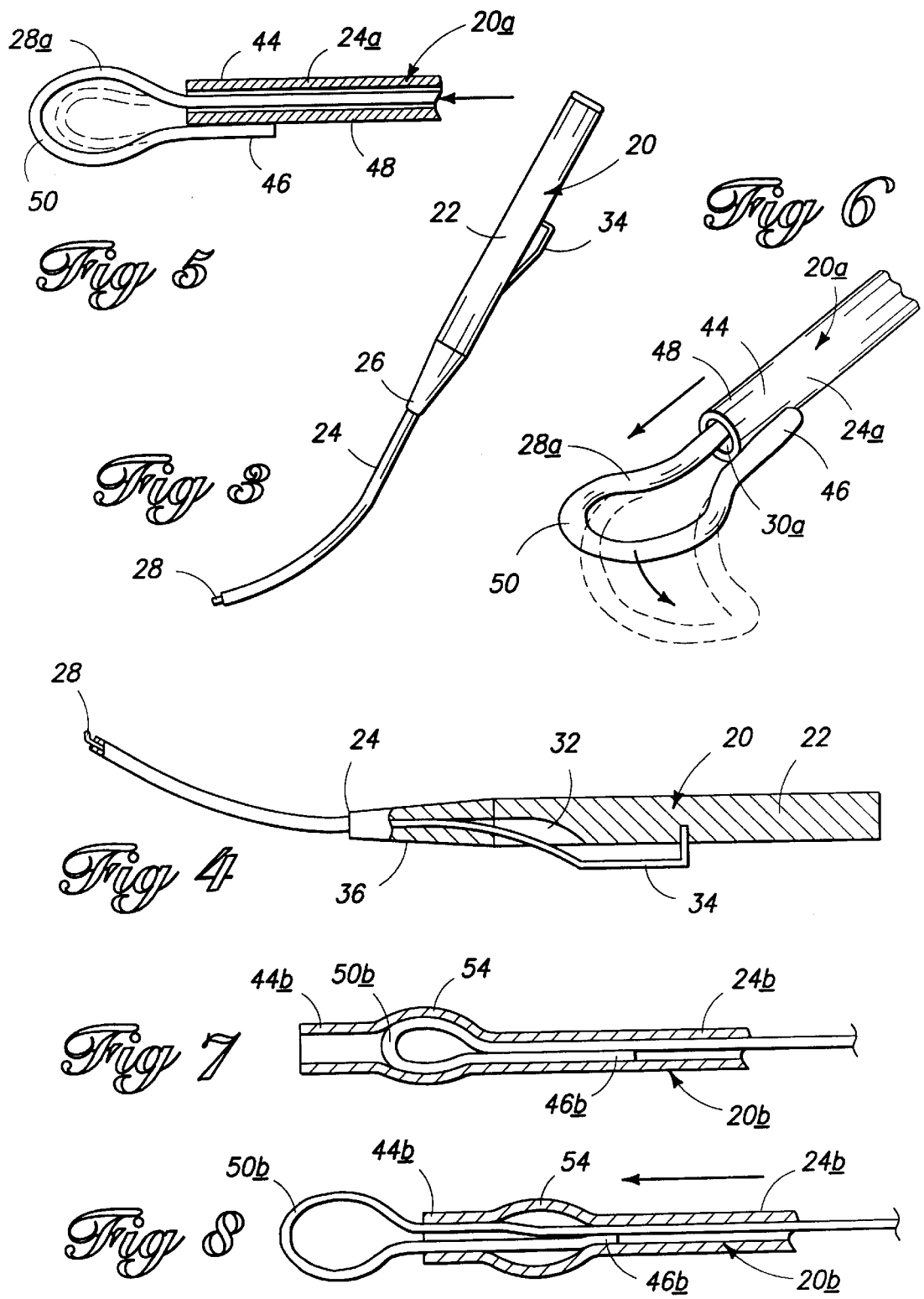

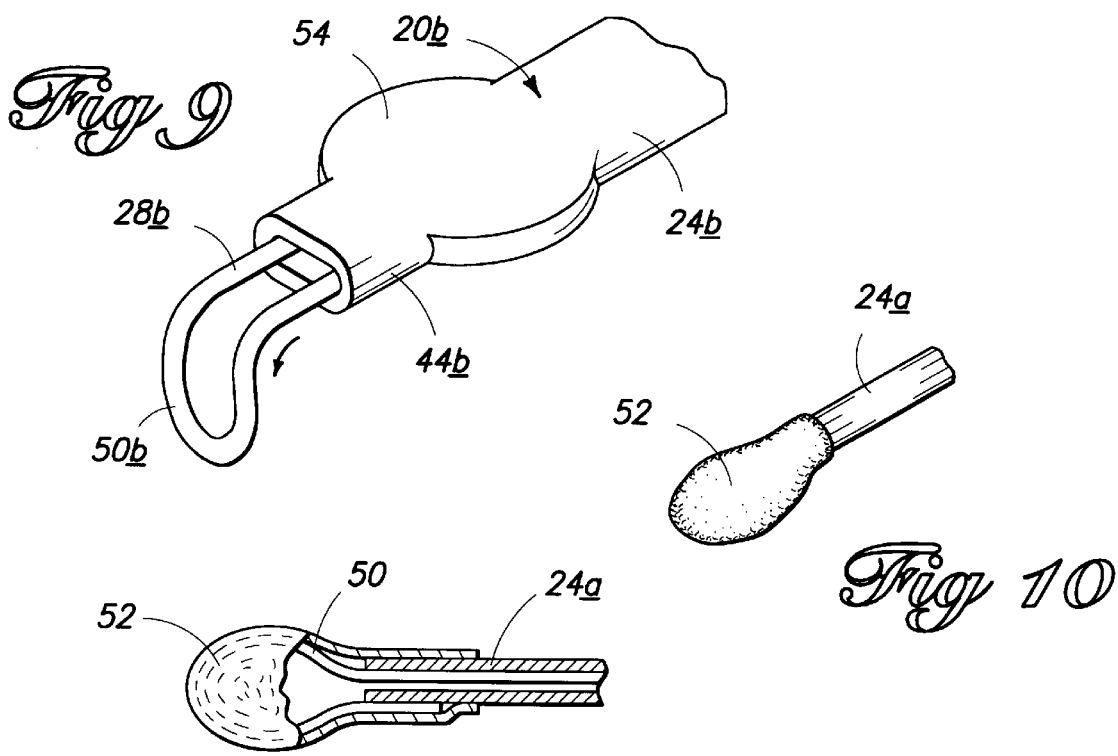
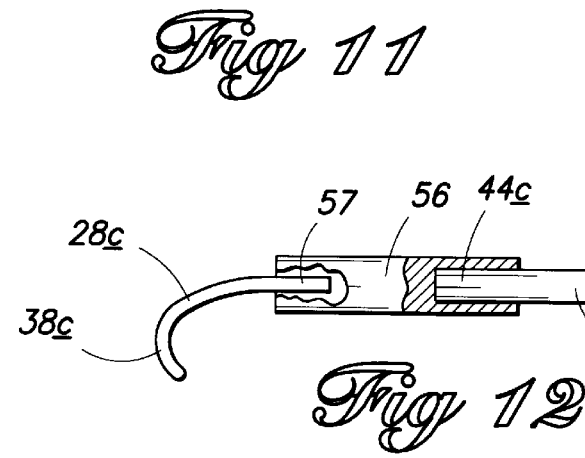
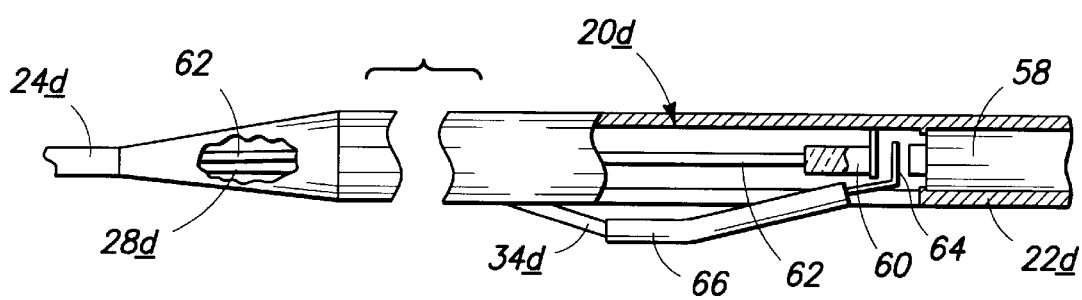

MEDICAL INSTRUMENT FOR REMOVING LUMEN OBSTRUCTIONS

BACKGROUND OF THE INVENTION

1. Field of the Invention

The present invention generally relates to medical instruments and more particularly to an improved medical instrument for removing obstructions from ear canals, nostrils and endotracheal tube airways.

2. Prior Art

An ear curette instrument is commonly used to remove cerumen and foreign bodies from ear canals Most such curettes have a long, stiff, relatively thick straight shaft of metal or plastic to the front of which is fixedly connected in a set position a relatively large wire loop or spoon of fixed size tilted at an angle to allow it to be positioned behind the cerumen or foreign material in the ear canal. The cerumen or foreign object is extracted by pulling it out of the ear canal as the instrument is withdrawn.

Certain problems are encountered with such instruments. Thus, the fixed angle and large cross sectional diameter of the instrument tip hinder the passage of the tip through the distal orifice with large otoscope specula. Such task is impossible when ear speculums of appropriate small size are used on infants and small children. Moreover, once the instrument tip is advanced beyond the otoscope speculum, it is difficult to avoid pushing the cerumen or foreign object deeper into the ear canal.

Proper alignment of the instrument tip by advancing it downward is very difficult due to the size of the otoscope head. In addition, the instrument is difficult to stabilize if the patient moves, thereby increasing the risk of abrasion or laceration of the ear canal or perforation of the ear drum. Such an instrument largely obstructs a clear view of the ear drum, walls of the ear canal and the cerumen or foreign object because of the large diameter of the instrument shaft, the fixed angle of the tip, the required angling of the tip and because the practitioner's hand blocks the view.

Problems similar to those described above are encountered when the instrument is used to remove foreign objects from the nasal passages.

A suction catheter is normally used to remove secretions and mucous from the lumen of an intubated endotracheal tube. However, when the mucous hardens into a large mass suction may be incapable of removing it and removal of the endotracheal tube and re-intubation may be required, a potentially harmful and stressful procedure, especially for young patients.

Accordingly, there is a need for an improved instrument which can easily and successfully remove cerumen and foreign objects from ear canals, foreign objects from nasal passages and hardened secretions from endotracheal tube airways.

SUMMARY OF THE PRESENT INVENTION

The improved medical instrument of the present invention satisfies all the foregoing needs. Thus, the instrument includes an easily held and manipulated handle, with or without an internal light source. The handle is connected to an elongated tube extending forwardly thereof. A thin elongated wire, which for the purposes of the present invention can be in the form of a single or multiple wire strand or a thin narrow sheet, is disposed within the tube and has a curved front end which forms a scoop. The wire and tube in one embodiment are removeable as a unit from the handle.

In another embodiment of the instrument of the present invention, the wire front end or tip can be advanced toward the material to be removed from the lumen without advancing the handle. Thus, the view of the lumen remains clear of the practitioner's hand.

As the tip advances over the material to be removed, the movement vector of the apex of the tip describes an arc, allowing the tip to encircle, trap and easily remove the material from behind it, without danger of injuring surrounding tissue. In this embodiment the tip is wholly or partially retractible within the tube. As the tip advances it gradually expands into a loop of controlled size. Downward angulation and expansion of the tip are developed behind the material to be removed, not in front of it. Advancing and retracting of the wire can be accomplished by connecting it to a manually operated spring disposed in and extending outwardly of the handle. The tube can be easily passed through a speculum and/or otoscope because in the retracted position the instrument tip is wholly enclosed in the instrument tube.

In a further similar embodiment, the tip is formed into a loop which is either fully retractible to a position within the tube which is elastic or is covered with a removeable sheath. In either case, the loop can be advanced and expanded under the control of the practitioner, and is more readily passable through a speculum or otoscope than is a conventional large size tip scoop.

Various other aspects of the improved instrument of the present invention are set forth in the following detailed description and accompanying drawings.

DRAWINGS

FIG. 3 is a schematic side elevation of the instrument of FIG. 1 showing the tip thereof almost fully retracted;

FIG. 4 is a schematic side elevation, partly in section, of the instrument of FIG. 3;

FIG. 5 is a schematic side elevation, partly in section, of the looped wire tip and front portion of the tube of a second preferred embodiment of the instrument of the present invention, the tip being shown in a partially expanded form;

FIG. 6 is a schematic perspective view of the tip and front portion of the instrument of FIG. 5, showing in dotted outline the angle, shape and size of the tip when it fully expands;

FIG. 7 is a schematic side elevation, partly in section, of the front portion of a third preferred embodiment of the improved instrument of the present invention, showing the tip thereof in fully retracted position within the tube thereof;

FIG. 8 is a schematic side elevation, partly in section, of the instrument of FIG. 7, shown with the tip thereof advanced and expanded in front of the tube thereof;

FIG. 9 is a schematic perspective view of the instrument of FIG. 7, shown with the tip thereof fully expanded and angled;

FIG. 10 is a schematic perspective view of a removeable cap disposed over the tip of the instrument of FIG. 5;

FIG. 11 is a schematic elevation, partly broken away and partly in section, of the cap of FIG. 10 in place on the tip of FIG. 5;

FIG. 12 is a schematic side elevation, partly broken away, of the front portion of the removeable tube and tip of a fourth preferred embodiment of the improved instrument of the present invention; and, FIG. 13 is a schematic side elevation, partly borken away and partly in section, of a fifth preferred embodiment of the improved instrument of the present invention.

DETAILED DESCRIPTION

FIGS. 1–4

Figure 1:
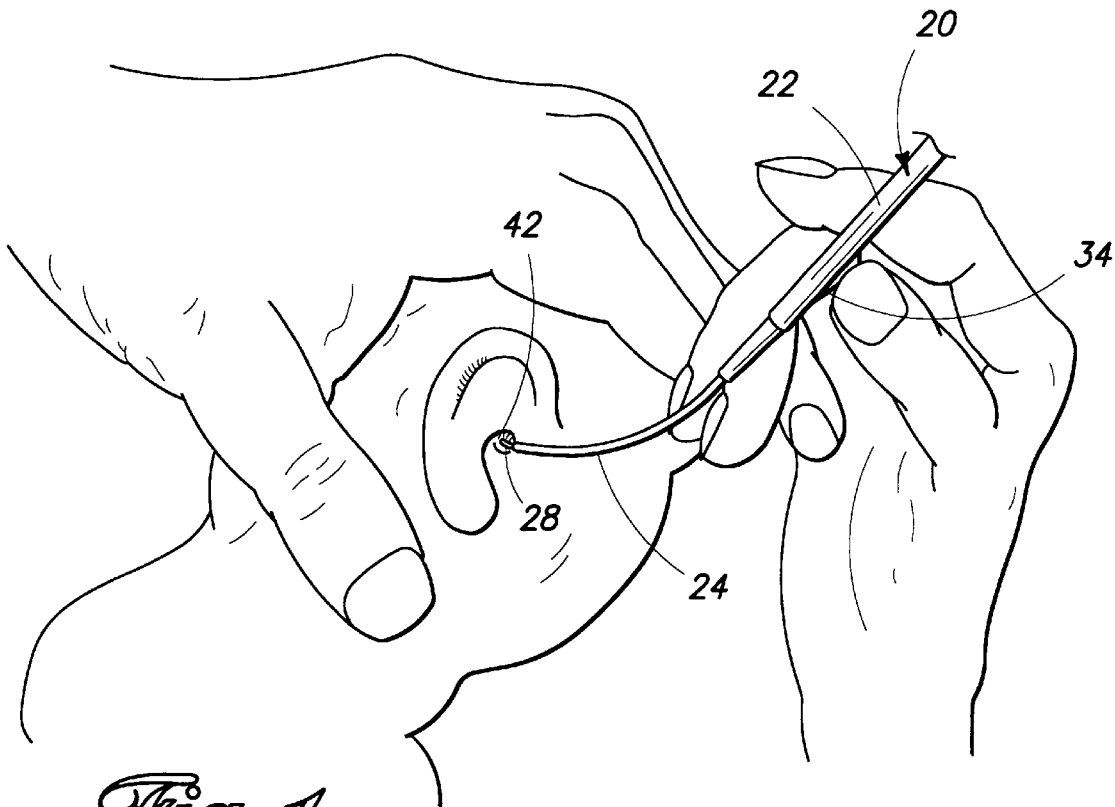
FIG. 1 is a schematic perspective view of a first preferred embodiment of the improved medical instrument of the present invention, showing it disposed just outside the entrance of an ear canal before advancing the tip of the instrument.
Figure 2:
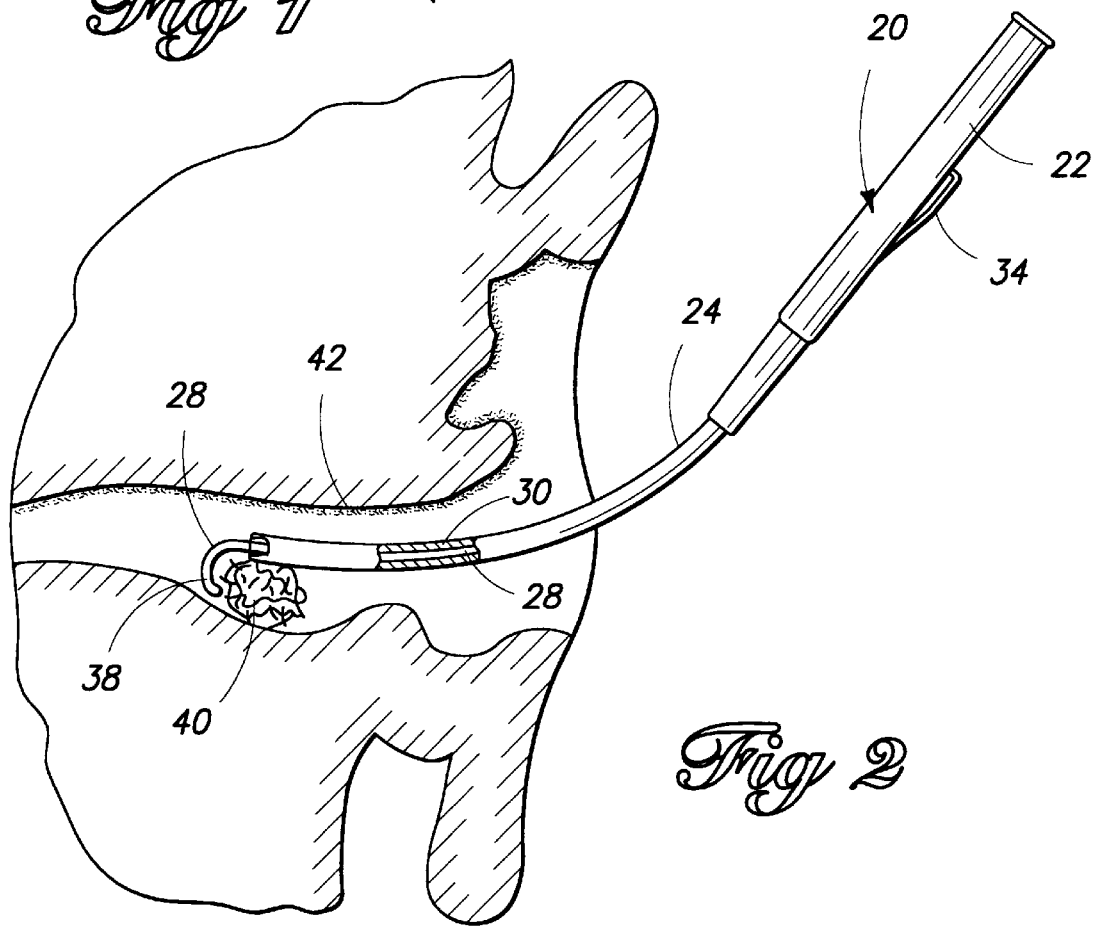
FIG. 2 is a schematic side elevation, partly in section and partly broken away, showing the instrument of FIG. 1 with the curved tip thereof disposed behind ear cerumen for ready removal thereof.

Now referring more particularly to FIGS. 1–4 of the drawings, a first preferred embodiment of the improved medical instrument for removing lumen obstructions is schematically depicted therein.

Thus, instrument 20 is shown which comprises, in combination, an elongated handle 22 to be held in the hand of the medical practitioner, an elongated sleeve or tube 24 connected to and extending from the front end 26 of handle 22, and a flexible resilient wire 28 disposed in a cavity 30 extending through tube 24 and a cavity 32 in handle 22 communicating with cavity 30. By wire 28 is meant, for the purposes of the present invention, a single or multiple strand wire or strip Wire 28 is connected to and may form part of a spring 34 which is disposed in cavity 32 of handle 22 and which extends to the exterior 36 of handle 22 to form means for controlling the position of wire 28 relative to tube 24. Spring 34 biases wire 28 into cavities 30 and 32. When, however, spring 34 is pressed toward handle 32 by the medical practitioner the front portion 38 of wire 28 is moved forward of tube 24 into an operative position for removing cerumen 40 from an ear canal 42.

Front portion 38 of wire 28 is prestressed so as to curve in a semi-circular arc or the like such as is shown in FIG. 1 when it is moved forward by spring 34 to a position forward of tube 24. This feature of wire 28 has several advantages. Thus, when front portion 38 of wire 28 lies wholly within tube 24, tube 24, which is of narrow diameter, can easily pass through an opening in an otoscope or the like and does not obscure the practitioner's view of the cerumen 40 to be removed from ear canal 42. Tube 24 itself may be somewhat curved, as shown in FIGS. 1–4, to more easily properly position tube 24 and wire 28 adjacent cerumen 40 or other obstruction to be removed from ear canal 42 without damaging surrounding structures.

An additional feature of wire 28 is that front end 38 thereof can be carefully moved forward by spring 34 to pass around behind the obstruction and form a scoop by which the cerumen 40 or other obstruction can then be easily removed from ear canal 42, instead of pushing cerumen 40 deeper into ear canal 42, as often occurs with conventional curettes. All this is accomplished without having the practitioner's hand move forward to block the view of the ear canal, as often also occurs with conventional curettes.

Tube 24, wire 28 and handle 22 can be of nay suitable material, such as metal, plastic or the like. Preferably, wire 28 is of metal. Instrument 20 is durable, inexpensive, reuseable and highly efficient for its intended purposes. It can be used to remove obstructions from nasal passages and endotrachial tube airways just as easily as described above for its application in removing obstructions from ear canals. Tube 24 and wire 28 are of sufficiently small size so that instrument 20 can be safely, painlessly and efficiently used to remove obstructions in small children and infants, as well as adults.

FIGS. 5, 6, 10 and 11

A second preferred embodiment of the improved medical instrument of the present invention is schematically depicted in FIGS. 5 and 6 and a cover for the same is schematically shown in FIGS. 10 and 11.

Thus, FIGS. 5 and 6 depict instrument 20a. Components thereof similar to those of instrument 20 bear the same numerals but are succeeded by the letter "a". Only front portion 44 of tube 24a with cavity 30a and front portion 38a of wire 28a are shown in FIGS. 5 and 6. The remainder of instrument 20a is substantially the same as instrument 20.

Wire 28a differs from wire 28 in that end 46 of wire 28a is rigidly connected to the outer surface 48 of tube 24a so that front portion 38a forms a loop 50 which expands in size as the moveable portion 52 of wire 28a is moved forward, as by a spring (not shown) in the handle (not shown) of instrument 20a, the spring and handle being substantially identical to spring 24 and handle 22, as previously described for instrument 20 of FIGS. 1–4.

It will be noted that as loop 50 expands in size it moves into the oblique orientation shown in dotted outline in FIG. 6 to facilitate positioning of loop 50 behind the obstruction to be removed by loop 50 which, in effect, forms a scoop of variable size. Since loop 50 before its expansion can be of relatively small size it can be easily passed through an opening in an otoscope or the like during use of instrument 20a.

In order to protect loop 50 against damage, contamination and the like, a removeable protective sheath 52 (FIGS. 10 and 11) can be slipped over loop 50 and removed therefrom when instrument 20a is to be used. Sheath 52 can be of stretchable rubber, plastic or the like.

FIGS. 7–9

A third preferred embodiment of the improved instrument of the present invention is schematically depicted in FIGS. 7–9. Thus, instrument 20b is shown. Components thereof similar to those of instrument 20 and/or 20a bear the same numerals but are succeeded by the letter "b".

Instrument 20b differs from instrument 20a only as follows:

a) Loop 50b has end 46b which extends into cavity 30b of front portion 44b of tube 24b;

b) Front portion 44b of tube 24b is expandable to accomodate the passage of loop 50b therethrough; and, c) Tube 24b has an expanded mid-portion 54 which houses loop 50b when instrument 20b is not in use, obviating the need for sheath 52 or the like.

Instrument 20b has substantially the other advantages of instruments 20 and 20a.

FIG. 12

A fourth preferred embodiment of the improved instrument of the present invention is schematically depicted in FIG. 12.

Thus, instrument 20c is shown. Components thereof similar to those of any of instruments 20, 20a and 20b bear the same numerals but are succeeded by the letter "c".

Instrument 20c is a simplified version of instrument 20 because of the following:

a) Front portion of tube 24c has a removeable and replaceable cap 56 which bears wire 28c;

b) Wire 28c has a permanently curved front end 38c, with the rear portion 57 of wire 28c fixed in cap 56 so that cap 56 and wire 28c can be removed from tube 24c as a unit; and, c) Tube 24c has no cavity therein, nor is there any cavity or spring in the handle (not shown) of instrument 20c.

When it is desired to use instrument 20c, tube 24c can be passed through an opening in an otoscope or the like and thereafter cap 56 with attached wire 28c can be fitted over tube 24c to the position shown in FIG. 12 before use of instrument 20c. Cap 56 and wire 28c can be rotated as a unit to the desired angle before obstruction removal is carried out.

FIG. 13

A fifth preferred embodiment of the improved instrument of the present invention is schematically depicted in FIG. 13. Thus, instrument 20d is shown. Components thereof similar to those of instrument 20 bear the same numerals but are succeeded by the letter "d".

Instrument 20d is substantially identical to instrument 20, except that instrument 20d has a light means disposed in handle 22d and operable by spring 34d. Thus, such light means, may include a battery 58 to power a light 60 connected to a fiber optic tube 62 which extends through cavities 30d and 32d to deliver light to the area of an obstruction to be removed by wire 28d.

When spring 34d is pressed to move wire 28d forward through tube 24d, the rear end 64 of spring 34d contacts battery 58 to complete the circuit to light 60 and cause it to go on. Spring 34d is sheathed in an electrically insulative sleeve 66 over the area of spring 34d which the practitioner pushes to operate instrument 20d. When depression of spring 34d is terminated, the electrical contact between light 60 and battery 58 ceases and light 60 automatically goes off.

Accordingly, instrument 20d has the advantages of instrument 20, plus the additional feature of illuminating the field of view for the practitioner when instrument 20d is being used.

Various other modifications, changes, alterations and additions can be made in the improved instrument of the present invention, its components and parameters. All such modifications, changes, alterations and additions as are within the scope of the appended claims form part of the present invention.

What is claimed is:

1. An improved medical instrument for removing lumen obstructions, said instrument comprising, in combination:

a) an elongated handle having a front portion, an opposite rear portion and a generally central cavity extending substantially the length of said handle;

b) an elongated tube connected to and extending from said front portion of said handle, said tube having a front portion, a rear portion and a cavity extending the length thereof and communicating with said handle cavity;

c) a wire extending through said handle and tube cavities and having a front portion and an opposite rear portion, said front portion comprising a loop projecting forwardly of said tube when said loop is in an operative position for scooping lumen obstructions; and, d) spring means connected to said rear portion of said wire and extending out from the exterior of said handle, said spring means biasing said front portion of said wire towards said tube but manually operable against said bias to extend said wire loop into an operative expanded position wherein said tube is elastic and wherein said loop is fully retractable into said tube.

2. The improved instrument of claim 1 wherein said loop is prestressed so that as said loop is extended into an operative expanded position said loop curves into a position which facilitates said scooping.

* * * * *